US008608654B2

(12) United States Patent
Carlberg et al.

(10) Patent No.: US 8,608,654 B2
(45) Date of Patent: Dec. 17, 2013

(54) METHOD AND SYSTEM FOR ACQUIRING PATIENT-RELATED DATA

(75) Inventors: Anders Carlberg, Malmö (SE); Niclas Olofsson, Malmö (SE)

(73) Assignee: Radiometer Medical ApS, Brønshøj (DK)

( * ) Notice: Subject to any disclaimer, the term of this patent is extended or adjusted under 35 U.S.C. 154(b) by 0 days.

(21) Appl. No.: 13/484,159

(22) Filed: May 30, 2012

(65) Prior Publication Data

US 2012/0310669 A1    Dec. 6, 2012

(30) Foreign Application Priority Data

May 31, 2011    (DK) .................................. 2011 00412

(51) Int. Cl.
*A61B 5/00*    (2006.01)
(52) U.S. Cl.
USPC .................................. 600/300; 705/2; 705/3
(58) Field of Classification Search
USPC ......................................... 705/2, 3; 600/300
See application file for complete search history.

(56) References Cited

U.S. PATENT DOCUMENTS

| 4,835,372 A | 5/1989 | Gombrich et al. | |
| 5,626,144 A | 5/1997 | Tacklind et al. | 128/725 |
| 2004/0019464 A1 | 1/2004 | Martucci et al. | |
| 2004/0102683 A1 | 5/2004 | Khanuja et al. | 600/300 |
| 2005/0192842 A1 | 9/2005 | Stawski et al. | 705/3 |
| 2009/0069642 A1 | 3/2009 | Gao et al. | 600/300 |

FOREIGN PATENT DOCUMENTS

| CA | 2 671 501 A1 | 7/2008 |
| JP | 10-500598 | 1/1998 |
| JP | 2002-297780 A | 10/2002 |
| JP | 2004-174068 A | 6/2004 |
| JP | 2010-512883 A | 4/2010 |
| WO | 2011/010232 A2 | 1/2001 |

OTHER PUBLICATIONS

International Search Report and Written Opinion dated Aug. 21, 2012 and Aug. 27, 2012, respectively, from counterpart PCT application.

*Primary Examiner* — Michelle Le
(74) *Attorney, Agent, or Firm* — Morgan, Lewis & Bockius LLP

(57) ABSTRACT

A method performed by a data processing system of registering patient-related data, the method including receiving, from a registration device, a set of identification data items and one or more identification time stamps, wherein each identification time stamp is associated with at least one of the identification data items, and the set of identification data items comprises a device identification data item identifying an electronic device and a patient identification data item identifying a patient; receiving, from the electronic device, patient-related data to be registered and an acquisition time stamp indicative of an acquisition time at which the patient-related data has been acquired; and associating the received patient-related data with an identified patient based on at least the received device identification data item, the received patient identification data item, the received one or more identification time stamps and the received acquisition time stamp.

22 Claims, 5 Drawing Sheets

METHOD AND SYSTEM FOR ACQUIRING PATIENT-RELATED DATA

The present invention claims the benefit of Danish Patent Application No. PA 2011 00412, filed in Denmark on May 31, 2012, which is hereby incorporated by reference.

BACKGROUND OF THE INVENTION

1. Field of the Invention

The present invention relates to methods, products, systems and devices for acquisition and processing of patient-related data, such as test and measurement results and/or other clinical data.

2. Discussion of the Related Art

Within the field of clinical analysis, a wide variety of electronic devices are known for the acquisition and registration of patient-related data. In particular, devices allow clinical personnel to acquire test and/or measurement results related to a given patient at a point of care. Such electronic devices include devices for performing various forms of clinical tests and/or analysis, such as the measurement of physiological parameters of a patient.

In modern clinical environments, such electronic devices are widely used, and tests are increasingly being moved from a central laboratory to the actual point of care (POC). Even though this trend has a number of advantages, it also involves a number of challenges.

For example, the operational environment in which POC electronic devices are operated is less controllable than the environment of a central laboratory, e.g., in terms of controlling the personnel operating the devices. Furthermore, any electronic device may be operated by a number of different operators during the course of a day.

The data acquired by an electronic device often needs to be transferred to and recorded by a central data processing system, e.g., a server system implementing a patient database. It is desirable that this transfer is performable securely, reliably and efficiently.

Because electronic devices are frequently used for acquiring data relating to different patients, it is desirable to reduce the risk of patient mix-up and to ensure that correct data is registered in a patient database.

U.S. Pat. No. 5,626,144 discloses a system for monitoring and reporting medical information of patients suffering from chronic diseases such as diabetes or asthma. This prior art system includes a stand-alone monitor for storing data records comprising measured values and time stamps and for transmitting the records to a remote reporting unit. The remote reporting unit includes a relational database that comprises patient records each including a unique ID code pairing a patient and a remote sensor. The database is updated when records are downloaded and it allows the generation of chronological reports of status information of a physiological characteristic. Hence, even though this prior art system allows the remote collection of data from a monitoring device used by an individual patient in the course of long-term management of a chronic disease, it remains a problem to reliably record patient-related data in a hospital or other healthcare facility where multiple electronic devices are frequently used by different operators and to obtain data related to different patients.

US 2003/0065653 discloses a system for storing and retrieving medical records. According to this system, when a medical device is first used on the system, its own identification (manufacturer, and device ID number) is automatically registered with the system. A patient receives an ID number, the first time the patient receives an ECG or is x-rayed by equipment that is registered with this prior art system. Thus, the first time a patient is examined via medical equipment of this system, a universal record of not only the equipment, but also the patient is automatically created. The patient is provided with a patient identification card, and from that point on, the patient identification card is "registered" within the system. Even though this system allows for a central registration of patients and medical devices, it requires the individual medical devices to be adapted for use with the system.

However, in many clinical environments, there is a large variety of types of electronic devices with varying capabilities, e.g., in terms of data management, processing power, etc. At the same time, it is desirable to keep the requirements imposed on the capabilities of electronic devices limited so as to be able to manufacture them at a reasonable cost.

Generally it is desirable to ensure the quality of the acquired data, and to be able to verify compliance with operating procedures at the clinic at which the electronic devices are operated.

SUMMARY OF THE INVENTION

Accordingly, the present invention is directed to a method and system for acquiring patient-related data that substantially obviates one or more of the problems due to limitations and disadvantages of the related art.

Features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a method performed by a data processing system of registering patient-related data, the method including receiving, from a registration device, a set of identification data items and one or more identification time stamps, wherein each identification time stamp is associated with at least one of the identification data items, and the set of identification data items comprises a device identification data item identifying an electronic device and a patient identification data item identifying a patient; receiving, from the electronic device, patient-related data to be registered and an acquisition time stamp indicative of an acquisition time at which the patient-related data has been acquired; and associating the received patient-related data with an identified patient based on at least the received device identification data item, the received patient identification data item, the received one or more identification time stamps and the received acquisition time stamp.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
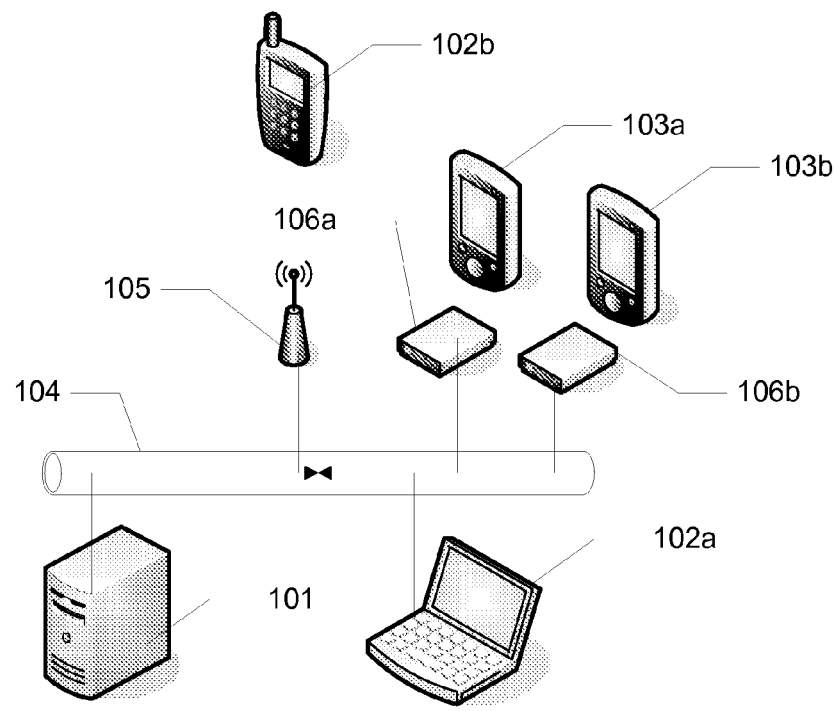
FIG. 1 is a schematic block diagram of an example of a system for acquiring patient-related data.

Reference will now be made in detail to embodiments of the present invention, examples of which are illustrated in the accompanying drawings.

Embodiments described herein provide a reliable association of acquired data to a particular patient without having to rely on patient data management or similar capabilities of the electronic device. As a such, the electronic device is not required to receive or store information identifying the patient.

In particular, embodiments of the method described herein provide a reliable association of patient-related data with a patient identifier, where the data has been acquired by an electronic device. It has been realized that this association may be reliably performed merely based on a device identification data item identifying the electronic device, a patient identification data item identifying the patient, a time stamp identifying the time at which the data acquisition occurred, and one or more time stamps associated with one or more of the identification data items, e.g., one or more time stamps indicative of the times the device and/or the patient have been registered.

Furthermore, embodiments of the method described herein allow for an establishment of a unique link between the acquired data and a patient even at a later point in time, e.g., if the acquired data is not transferred from the electronic device to the data processing system right away but rather at a later point in time. For example, some electronic devices that do not have any wireless communications interfaces may store the acquired data until the electronic device is connected to the data processing system via a wired connection, a docketing station, or some other suitable interface.

In embodiments of the method described herein, an establishment of an association between the received patient-related data and an identified patient is performed on the basis of at least the received device identification data item, the received patient identification data item, the received one or more identification time stamps and the received acquisition time stamp. Embodiments of the method described herein may be adapted to different standard operating procedures according to which health care personal may perform the data acquisition and patient registration. To this end, some embodiments of the association between the received patient-related data and the identified patient may compare the acquisition time with a first time identified by a first identification time stamp, and the association may then be based on a result of this comparison. For example, comparing may comprise determining whether the acquisition time lies within a predetermined data acquisition time interval determined from at least the first identification time stamp; and associating may comprise associating, if the acquisition time lies within the predetermined data acquisition time interval, the patient-related data with the patient identification data item. The data acquisition time interval may be a time interval starting at the first time and having a predetermined length. Hence, the first time may be a start trigger for a time interval during which acquired data will be associated to the registered patient. Alternatively, the data acquisition time interval may extend a first predetermined period prior to the first time and a second predetermined period after the first time. Hence, the acquisition time interval may be defined based on a single time stamp.

In some embodiments, receiving patient-related data to be registered and an acquisition time stamp further comprises obtaining a device identifier of the electronic device from which the patient-related data is received, and associating the received patient-related data with an identified patient is further based on the obtained device identifier of the electronic device from which the patient-related data is received. In particular, received patient-related data may be associated with a patient identifier that has been received in a set of identification data items including a device identification data item which matches the obtained device identifier of the electronic device from which the patient-related data has been received. Hence, the association based on time stamps described herein may even be reliably performed when different electronic devices are concurrently used for acquiring patient-related data.

Accordingly, associating the received patient-related data with an identified patient may comprise determining one or more received sets of identification data items each comprising a device identification data item that matches the obtained device identifier of the electronic device from which the patient-related data has been received, and associating the received patient-related data with the patient identification data item of one of the determined sets of identification data items based on at least the received one or more identification time stamps and the received acquisition time stamp.

In some embodiments, receiving a set of identification data items and one or more identification time stamps comprises receiving at least the first and a second identification time stamp, the second identification time stamp identifying a second time, and the data acquisition time interval is a time interval starting at the first time and ending at the second time. Hence, the data acquisition time interval is determined by two time stamps associated with respective identification data items. In particular, the first and/or the second time may be an identification time at which one of the identification data items has been obtained. Hence, the start and/or the end of the data acquisition time interval is defined by a registration event, e.g., by the operator scanning or otherwise registering the patient, the electronic device, and/or the like. Consequently, the acquisition time interval is defined by the actual registration process and automatically adapted to the chosen registration procedure and speed.

In some embodiments, determining the data acquisition time interval may comprise determining the data acquisition time interval as a time interval from an earliest one to a latest one of the identification times indicated by the received set of identification time stamps. Hence, the association of the acquired data is based on a time interval established by the time interval between an initial registration of one of the identification data items, e.g., the device identification data item, and the registration of the last one of the set of identification data items, e.g., the patient identification data item. Hence, the device identification data item, the patient identification data item, and optionally additional identification data items such as an operator identification data item, may be registered in any order. The earliest and the latest of the registrations define a time interval that is subsequently used by the data processing system to associate the acquired data with a given patient. Accordingly, as long as the operator performs the registration of at least one of the identification data items prior to the data acquisition, and the registration of at least another one of the identification data items after the data acquisition, the data processing system may uniquely associate the acquired data with a given time interval, and thus with the corresponding patient identification data item.

The first and/or the second time may be a time at which a predetermined trigger event has occurred. Here, the start and/or end of the data acquisition time interval may be determined by a predetermined trigger event, e.g., a predetermined operator input to the registration device, pressing a button, obtaining one of the identification data items, etc. or a combination thereof. Other examples of such an event include the receipt of a message by the registration device from an external system, e.g., a host system. Yet another example of such an event may be the expiry of a timer of the registration device.

The device identification data item and the patient identification data item are comprised in a set of identification data items, thus allowing them to be associated with one another as belonging to the same set, i.e., the same data acquisition event. In some embodiments, the data processing system may receive the set of identification data items as identification data items that are explicitly associated with another, e.g., by receiving a common data record including the set of identification data items. Alternatively, in some embodiments, receiving the set of identification data items comprises receiving a plurality of identification data items (which may not yet be explicitly associated with one another as belonging to respective data acquisition events) and determining the set of identification data items from the received plurality of received identification data items as a set of identification data items associated with the first identification time stamp. For example, the data processing system may identify a (sub-)set of identification data items to be associated with a common data acquisition event based on the relative timing of the individual registrations of identifiers and/or based on the sequential order of the individual registrations, and/or whether or not a complete set of a number of required identifiers has been registered, e.g., a patient identifier, a device identifier, and an operator identifier. Hence, the method described herein may be adapted to different capabilities of registration devices and easily matched to different standard operating procedures.

As mentioned above, the objects identified by the identification data items of the identification data items include the electronic device and the patient to which the patient-related data relates. In some embodiments, the set of identification data items may further comprise an operator identification data item identifying an operator of the electronic device, thereby increasing the safety, quality, and compliance of the registration process by allowing the system to verify whether the operator is authorized and/or trained to operate the electronic device.

The identification data items may be embodied as any suitable data structure indicative of an object—e.g., a patient, and electronic device, an operator, or the like—to be identified. For example, the identification data item may comprise a suitable identifier for identifying an object. Preferably, the identifier uniquely identifies an object. In addition to an identifier, the identification data item may comprise additional information such as a time stamp indicative of a registration time at which the identifier has been obtained, i.e., the time at which the respective object has been registered.

In some embodiments, receiving an acquisition time stamp from the electronic device further comprises receiving, from the electronic device, a control time stamp indicative of a current time determined by the electronic device, and correcting the acquisition time stamp based on a comparison of the control time stamp with a current time determined by the data processing device. Hence, even if the acquisition time may be determined by the electronic device based on an internal clock that may not be synchronised with the time registered by the data processing system, the data processing system may correct the received time stamp so as to be consistent with the time registered by the data processing system.

Aspects of the present invention relate to different aspects including the method described above and in the following, corresponding apparatus, systems, and products, each yielding one or more of the benefits and advantages described in connection with the above-mentioned method and/or one of the other aspects, and each having one or more embodiments corresponding to the embodiments described in connection with the above-mentioned methods and/or one of the other aspects. In particular, embodiments of a data processing system are disclosed for performing the method described above and in the following. The data processing system may be a suitably programmed computer such as a server computer, a desktop computer, and/or the like, and/or a data processing system comprising several computers, e.g., computers connected with each other via a suitable computer network.

Furthermore, embodiments of a system for acquiring patient-related data are disclosed wherein the system comprises a data processing system, an electronic device and a registration device as described herein. The electronic device and registration device may comprise any device including a processor for data processing. The electronic device and registration device may comprise any electronic equipment, portable radio communications equipment, and other handheld or portable devices, personal computers or other computers or data processing systems. Embodiments of the electronic device and/or the registration device may further comprise a respective communications interface adapted for communicating data to the data processing system, e.g., via a wired or a wireless communications channel, such as a local area network, a wireless local area network, a wide area network, an internet, a telecommunications network such as a cellular communications network, a short range wireless communications interface, a serial or parallel interface, a USB interface, a Bluetooth interface, and/or the like.

The electronic device may further comprise data acquisition unit for acquiring patient-related data such as test data, measurements of physiological parameters, detected types and/or dosages of a medication, etc. Embodiments of the registration device may further comprise an input for receiving identifiers, for example, the input may include a reader for reading a machine readable code such as a barcode scanner, a reader for reading radio-frequency identification (RFID) tags or labels, a user-interface allowing manual input of identifiers, a camera, or any other suitable input. Generally, embodiments of the electronic device may include a medical device, such as a clinical instrument for performing clinical tests and/or analysis, a drug dispensing device, and/or another medical device for clinical use.

The portable radio communications equipment may include all equipment such as mobile terminals, e.g., mobile telephones, pagers, communicators, electronic organisers, smart phones, personal digital assistants (PDAs), handheld computers, or the like.

The electronic device and/or the registration device may further comprise respective storage media or computer readable media, e.g., a hard disc, an optical disc, a compact disc, a DVD, a memory stick, a memory card, an EPROM, and/or the like. The electronic device may further comprise a device for establishing a current time, e.g., an internal clock and/or by receiving time information from an external source such as the data processing system and/or a communications network.

It is noted that the features of the methods described herein may be implemented in software and carried out on a data processing system or other processing system caused by the execution of program code means such as computer-executable instructions. Here and in the following, the processor may comprise any circuit and/or device suitably adapted to perform the above functions. In particular, the processor may comprise general- or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

According to another aspect, a computer program comprises program code means adapted to cause a data processing system to perform the steps of the method described herein, when the computer program is run on the data processing system. For example, the program code means may be loaded in a memory, such as a RAM (Random Access Memory), from a storage medium or from another computer via a computer network. Alternatively, the described features may be implemented by hardwired circuitry instead of software or in combination with software.

FIG. 1 shows a schematic block diagram of an example of a system for acquiring patient-related data. The system comprises a server computer 101 or other suitable data processing system suitably programmed to store and maintain medical records of patients, e.g., in a suitable database system. The server computer 101 is connected to a computer network 104, e.g., a local area network (LAN). The computer network 104 may comprise a wireless access point 105 or other suitable wireless interface device allowing electronic devices to wirelessly connect to the computer network 104. The system further comprises a number of registration devices 102a, 102b, connected or connectable to the computer network 104. In the example of FIG. 1, the system comprises two registration devices, one registration device 102a being connected to the computer network via a wired connection, e.g., via a local area network interface circuit, and one registration device 102b being wirelessly connected, e.g., via wireless access point 105, to the computer network 104. It will be appreciated, however, that embodiments of the system described herein may comprise any number of registration devices, each being connectable to the computer network via a suitable communications interface. The system further comprises a number of electronic devices 103a and 103b. In the example of FIG. 1, the electronic devices are connectable to the computer network via respective docking stations 106a and 106b. However, it will be appreciated that embodiments of the system described herein may comprise any number of electronic devices. The electronic devices may be identical with each other or different from each other, and they may be connectable to the computer network in a variety of different ways, e.g., by a wired and/or wireless connection. Each of the registration devices may be a suitable portable or stationary computer or other computing device, such as a laptop computer, a desktop computer, a handheld computer such as a PDA, a Smartphone, a tablet computer, etc.

Figure 2:
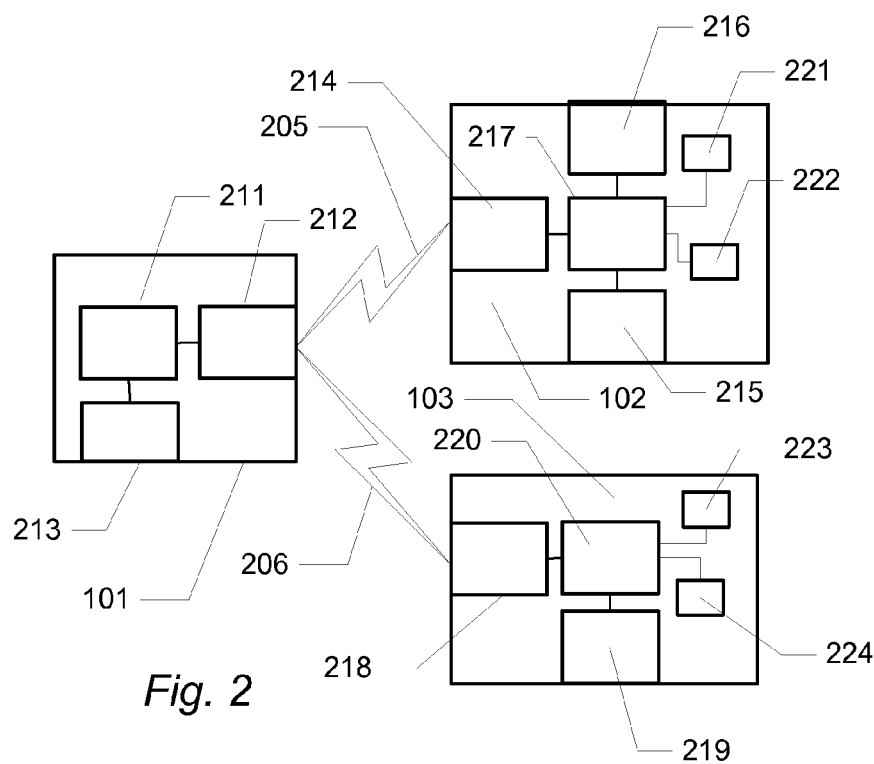
FIG. 2 is a schematic functional block diagram of an embodiment of a system for acquiring patient-related data.

FIG. 2 is a schematic functional block diagram of an embodiment of a system for acquiring patient-related data. The system comprises a data processing system 101 (in the following also referred to as host system) suitably programmed to store and maintain medical records of patients, a registration device 102, and an electronic device 103. As mentioned above, even though FIG. 2 only illustrates a single registration device and a single electronic device, embodiments of the system may include respective pluralities of these devices. It will also be appreciated that the functionality of the host system 101 may be distributed among a plurality of physical devices, e.g., a plurality of server computers and/or a plurality of database systems.

The registration device 102 is connectable to the host system 101 via a suitable communications link 205 allowing data communication between the host system 101 and the registration device 102. To this end, the registration device and the host system comprise respective communications interfaces 214 and 212, allowing data communication via the communication link 205. Similarly, the electronic device 103 is connectable to the host system 101 via a suitable communications link 206 allowing data communication between the host system 101 and the electronic device 103. To this end, the electronic device and the host system comprise respective communications interfaces 218 and 212, allowing data communication via the communication link 206. The communications links 205 and 206 may be implemented using the same or different communications technologies, e.g., the same or different computer networks. Accordingly, the communications interface 212 of the host system may be embodied as a single interface device or as a plurality of interface devices supporting respective communication technologies, e.g., a network adapter for a wired connection to a local area network and a radio-frequency transmitter for connecting the host computer with other devices via a short-range radio-network. Generally, examples of suitable communication interfaces include a wired or wireless network adapter, a radio-frequency communications interface allowing communication via a telecommunications network such as a cellular communications network, a radio-frequency communications interface allowing communication via a short-range wireless communications interface, a serial or parallel interface adapter, a USB port, and/or the like.

The host system 101 further comprises a processing unit 211, such as a suitably programmed CPU of a computer or other suitable processing system, communicatively coupled to the communications interface 212. The host system 101 further comprises a data storage device 213 communicatively coupled to the processing unit 211, e.g., a database system or other data storage device for storing patient related data.

The registration device 102 comprises a processing unit 217 such as a suitably programmed CPU of a computer or other suitable processor, communicatively coupled to the communications interface 214. The registration device further comprises a data input unit or circuitry 215 for receiving identification data. The data input unit 215 is communicatively connected with the processing unit 217. Examples of the data input unit or circuitry include a reader for reading a machine-readable code such as a barcode scanner, a reader for reading radio-frequency identification (RFID) tags or labels, a user-interface allowing manual input of identifiers, a camera, or any other suitable input. The registration device may further comprise a user-interface 216, e.g., a display allowing the registration device to present output to a user of the registration device, e.g., by a graphical user interface. The registration device may further comprise a timer circuit 221, e.g., a clock or other suitable functionality for determining the current time, and a suitable data storage device 222 for storing registration data received via the data input unit, e.g., a RAM, an EPROM, a hard disk, etc.

The electronic device 103 comprises a processing unit 220, such as a suitably programmed microprocessor or other suitable processing system, communicatively coupled to the communications interface 218. The electronic device 103 further comprises a data acquisition device 219 communicatively coupled to the processing unit 220 for acquiring patient-related data such as test data, measurements of physiological parameters, detected types and/or dosages of a medication, etc. The registration device may further comprise a timer circuit 223, e.g., a clock or other suitable functionality for determining the current time, and a suitable data storage device 224 for storing data acquired by the data acquisition device 219, e.g., a RAM, an EPROM, a hard disk, etc. Examples of an electronic device include a meter or analyzer for measuring patient-related data, e.g., a blood glucose meter, a blood gas analyser, an analyzer for measuring cardiac, coagulation, infection and/or pregnancy markers, and/or the like.

Embodiments of operating a system for acquiring patient-related data, e.g., a system as described in FIG. 1. and/or 2, will now be described in more detail.

Figure 3:
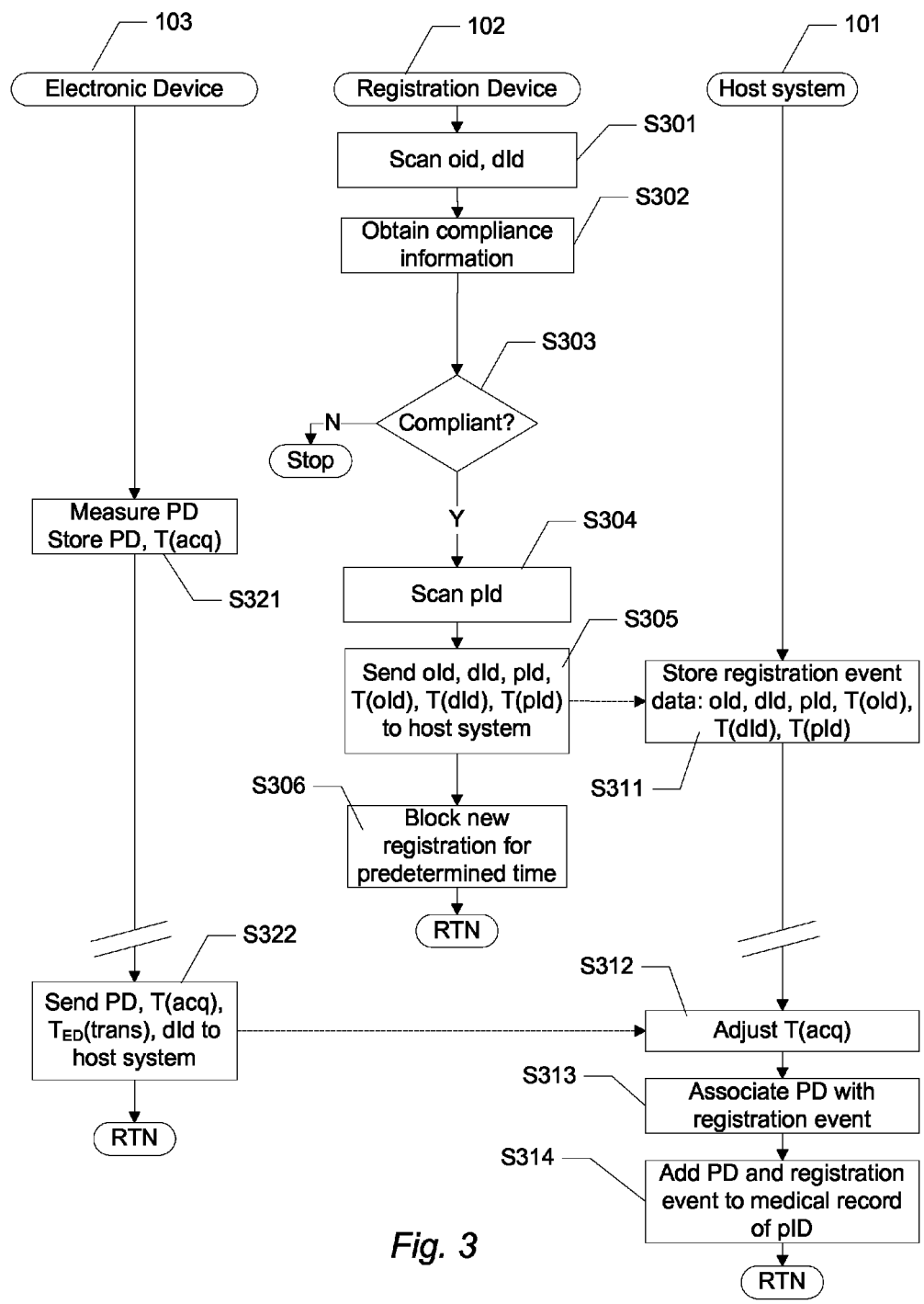
FIG. 3 is a flow diagram of an example of a method of acquiring patient-related data.

FIG. 3 shows a flow diagram of an example of a method of acquiring patient-related data. The process is performed by a system comprising a host system 101, a registration device 102, and an electronic device 103, e.g., as described in connection with FIGS. 1 and/or 2.

The process may be regarded as comprising two sub-processes, a first one performed by the registration device and the host system, and a second sub-process performed by the electronic device and the host system. The first sub-process comprises steps S301-S306 and step S311, while the second sub-process comprises steps S321-S322 and steps S312-S314.

The first sub-process is initiated in step S301 by the registration device 102 obtaining an operator identifier oId and a device identifier dId, the operator identifier identifying the operator of the electronic device 103, and the device identifier identifying the electronic device 103. The operator may be a nurse or other health care professional authorized to operate the electronic device 103. For example, the registration device may obtain the identifiers by scanning respective barcodes associated with the operator and the electronic device, respectively. For example, the operator may carry an identification card having printed on or otherwise applied to it a barcode, and the electronic device may have applied to it a label carrying a barcode. It will be appreciated that the electronic device may obtain the identifiers in any other suitable way, e.g., by RFID tags attached to the electronic device and the operator's clothes or an ID card. The registration device may be a portable device carried by the operator. Alternatively, the registration device may be a stationary device, e.g., located in a room of a hospital used for examining patients or where samples are obtained from patients. The registration device further registers the time T(oId) at which the operator identifier has been obtained, and the time T(dId) at which the device identifier has been obtained. The registration device associates the registered times with the respective obtained identifiers and may store the identifiers with their associated times in a local memory of the registration device, e.g., as respective identification data records, e.g., record comprising an identifier and an associated time stamp. The registration device may acknowledge a successful scan, e.g., by generating an audible sound and/or by displaying a suitable message on a display of the registration device, e.g., "Welcome Nurse B" in response to scanning the operator ID of nurse B.

In step S302, based on the obtained identifiers, the registration device obtains compliance information indicative of a compliance status of the electronic device 103 and/or a compliance status of the operator, e.g., information as to whether operation of the electronic device by the operator is in compliance with administrative rules of the hospital or health care centre at which the process is performed. For example, the electronic device may obtain information about the time remaining until the next required calibration or maintenance of the electronic device, and/or authorization information indicating whether the operator is authorized (e.g., qualified and properly trained) to operate the electronic device. The registration device may obtain the compliance information from a local compliance database stored in the registration database. For example, the local compliance database may regularly, e.g., daily, be updated by synchronising a central compliance database which may reside on the host system 101 or another suitable data processing system. Alternatively the registration device may obtain the compliance information from an external system, e.g., the host system 101. To this end, the registration device may communicate a compliance query including the operator identifier and/or the device identifier to the external system, e.g., to the host system 101 via communications link 205. The external system may return a compliance response indicative of whether operation of the electronic device by the operator is in compliance with the administrative rules of a hospital.

In step S303, the registration device determines, based on the obtained compliance information, whether operation of the electronic device by the operator is compliant with current administrative rules. If this is not the case, the registration device informs the operator (e.g., by an audible signal, a display of a suitable error message, and/or the like) about the lack of compliance, and terminates the process. Otherwise, the process proceeds at step S304, optionally after displaying the obtained compliance information on a display of the registration device, optionally together with additional information, e.g., when the next calibration of the device is due, when the operator is scheduled to receive further training in respect of the device, etc. For example, the device may display: "OK, You are certified for device X until May 17, 2011, QC: OK—next QC before May 12 07:00. CAL: OK—next CAL before May 11 17:00". It will be appreciated that, in some embodiments, the process may not include the compliance test of steps S302 and S303, i.e. the process may directly proceed from step S301 to step S304. In yet other embodiments, a determination of lack of compliance may merely result in a warning message without termination of the process. It will be appreciated that, in embodiments that do not include a compliance test of the authorization of the operator, the process may not require obtaining of the operator identifier.

In step S304, the registration device obtains a patient identifier pId identifying a patient from which the operator intends to acquire (or already has acquired) patient-related data using the electronic device 103. For example, the registration device may obtain the patient identifier in a similar fashion as the operator and device identifiers. To this end, the patient may carry or wear a wrist band, an ID card, or the like, including the identifier, e.g., in the form of a barcode and RFID tag, or the like. It will be appreciated that the patient identifier may also be an identifier identifying another object (e.g., a hospital bed) that is uniquely associated with the patient. The registration device further registers the time T(pId) at which the patient identifier has been obtained, and associates the registered time with the obtained patient identifier. The registration device may store the patient identifier with its associated time in a local memory of the registration device, e.g., as a patient identification data record comprising the patient identifier and an associated time stamp. The registration device may acknowledge a successful scan, e.g., by generating an audible sound and/or by displaying a suitable message on a display of the registration device, e.g.: "Patient ID: 1236556. Name: Peter Hansen Sex: Male."

In step S305 the registration device sends the patient identifier, the device identifier, and the operator identifier together with the respective associated time stamps indicative of the times at which the respective identifiers have been obtained to the host system 101, e.g., in the form of respective identification data records described above. For example the registration device may forward the identifiers and time stamps to the host system via communications link 205 of FIG. 2. Alternatively to forwarding all identifiers and time stamp in a single transmission, the registration device may forward the operator identifier and the device identifier, including their associated time stamps, to the host system immediately after the registration device has obtained the respective identifier, thereby avoiding the need for internally storing the identifiers and time stamps. Hence, in such an embodiment, the registration device at this point only needs to send the patient identifier and the associated time stamp to the host system. In an embodiment, where the registration device forwards each identifier to the host system immediately after the registration device has obtained the identifier, the registration device may not need to generate and forward a time stamp associated with the identifier. In such an embodiment, the host system may generate and store a suitable time stamp upon receipt of each identifier.

In step S311, the host system receives and stores the registration identifiers and associated time stamps. In one embodiment, the host system may store the identifiers as separate identification data records, each comprising an identifier and an associated time stamps. It will be appreciated that the identification data records may comprise additional information, e.g., an identifier identifying the registration device from which the identifier has been received. For example, the registration device may transmit such an identifier identifying the registration device together with the identifiers. In alternative embodiments, the host system may store the identifiers in a data record identifying a registration event where each registration event comprises a predetermined set of identifiers. In the present example, this set of identifiers may comprise the operator identifier, the device identifier and the patient identifier. Each registration event may further comprise one or more time stamps, e.g., a time stamp associated with one of the identifiers, or respective time stamps associated with some or each of the identifiers. In both embodiments, the set of identifiers comprising the patient identifier the operator identifier, and the device identifier are related to a common registration event.

After sending the identifiers and their associated time stamp, the process continues at step S306 where the registration device prevents the scanning/obtaining of additional identifiers for a predetermined time-out period, thereby providing a minimum time interval separating the time stamps associated with identifiers that relate to different registration events. For example, the registration device may prevent registration of further identifiers for a period sufficiently long to allow the host system to reliably associate measurement events and registration events, as will be described in greater detail below. Generally, the duration of the time-out period may depend on the lowest accuracy and resolution of the time stamps generated by any of the registration devices and the electronic devices of the system. For example, when the resolution of time stamps is minutes, the registration device may prevent registration of further identifiers for a period chosen between 1 min. and 3 min. During that period, the registration device may display a message requesting the operator to await the end of the time-out. The registration device may even display a countdown indicating the remaining time-out period. In some embodiments, the registration device may allow the operator to override the time-out and/or to cancel the previous registration event and to immediately start a new registration event. In the latter case, the registration device may send a request to the host system requesting deletion of the latest set of identifiers received by the host system from the registration device. In some embodiments, the prevention of obtaining additional identifiers for a pre-determined time-out period may be omitted. Instead, when the process obtains the device identifier dId in step S301, the process may determine the time resolution with which the identified device determines time stamps (e.g., by querying a database of devices using the device identifier as a key). If the time elapsed since the most recent previous scanning/obtaining of the same device identifier is smaller than the time resolution of the electronic device, the process may stop with a suitable error message or perform another suitable step, e.g., continue but display a warning message.

The second sub-process is initiated by the electronic device 103 obtaining patient-related data PD in step S321 and generating a corresponding time stamp T(acq) associated with the patient-related data and indicative of the time at which the patient-related data has been obtained. For example, if the electronic device is a measuring device, e.g., for measuring one or more physiological parameter of the patient, the patient-related data may comprise one or more measured values indicative of the one or more physiological parameters. Similarly, if the electronic device is a dispensing apparatus, e.g., for dispensing predetermined amounts of medicine, the patient-related data may include the type and/or amount of dispensed medicine. The electronic device may acknowledge successful data acquisition, e.g., by generating an audible sound and/or by displaying a suitable message on a display of the electronic device, such as "<time stamp as recorded>Your result will be transmitted to the patient record next time the instrument is placed in the docking station."

In subsequent step S322, the electronic device 103 forwards the acquired data PD, the associated time stamp T(acq) to the host system 101. The electronic device may further transmit its own device identifier dId together with the patient-related data PD and the time stamp T(acq), thus allowing the host system to identify the electronic device from which the patient-related data originates. Alternatively, the host system may obtain the device identifier of the electronic device that has forwarded the patient-related data in a different way, e.g., by assigning different communication ports of the host system to different electronic devices, and by determining (by the host system) over which port the patient related data has been received. The electronic device may forward the acquired patient-related data immediately after it has been acquired or at a later point in time, e.g., several minutes or even hours later. An immediate transmission may be possible, if the electronic device comprises real-time communications capabilities, e.g., via a wireless communications link between the electronic device and the host system. A delayed transmission may occur when the electronic device only communicates with the host system periodically, e.g., at regular or even irregular time intervals between opportunities to transmit data. For example, many electronic devices do not comprise wireless communications capabilities. Examples of such devices include hand-held meters that may be placed in a cradle or docking station which is connected to a computer network. Such devices may only be able to transmit data when placed in its cradle or docking station, e.g., after the operator has acquired a large amount of data, typically from different patients and over an extended period of e.g., several hours or even an entire day. Other examples may include meters that store data on a storage medium, e.g., a memory card, such that communication of the acquired data involves the operator removing the storage medium from the meter and inserting it in a card reader that is connected to the host system.

In any event, when the acquired patient-related data is forwarded to the host system, the host system may store the received patient-related data and associated time stamp. In some embodiments, the host system may adjust (step S312) the received time stamp T(acq) for any detected inaccuracy of synchronisation between the time as measured by the electronic device, and the time measured at the host system. To this end, the electronic device may further transmit a reference time stamp $T_{ED}(trans)$ together with the patient-related data PD and the time stamp T(acq), where the reference time stamp may be indicative of the current time (as determined by the electronic device) at which the electronic device transmits the patient-related data. Upon receipt of the data, the host system may compare the received reference time stamp with the local time of receipt $T_{HS}(rec)$ determined by the host system. The host system may calculate the difference $DT=T_{HS}(rec)-T_{ED}(trans)$ and, assuming that the difference DT is due to a lack of synchronization of the internal clocks of the electronic device and the host system, adjust the time stamp T(acq) accordingly, e.g., according to T(acq)->T(acq)+DT. Alternatively, the host system, and/or the registration device may include functionality allowing the host system or the registration device to set the clock of the electronic device, e.g., by sending a suitable request to the electronic device, if the electronic device supports such requests. Yet alternatively, for those devices where it is not possible to adjust the clock, the host system or registration device may warn the operator about the mismatch allowing the operator to manually adjust the time on the electronic device.

It will be appreciated that the first- and second sub-processes are asynchronous in the sense that there is no direct link between the initiation of both processes. Each process is normally initiated by the operator when the operator initiates registration of the first identifier (step S301) and when the operator initiates the obtaining of the patient-related data (step S321), respectively. Hence, the system cannot control the relative timing of the data acquisition step S321 and steps S301 and S304 at which the identifiers are obtained. It will be appreciated that the order of these steps will often be prescribed by standard operation procedures of the hospital or health care center which may prescribe a predetermined order of steps to be performed by the operator. Hence, the host system may receive a plurality of patient-related data items obtained at different times by the same electronic device but related to different patients.

Accordingly, in subsequent step S313, the host system associates the patient related data to a patient identifier, based on the device identifier dId (e.g., based on a comparison of the device identifier obtained from the electronic device that has forwarded the patient-related data with the device identifier that was registered in connection with the registration of the patient identifier), on the (optionally adjusted) time stamp T(acq) of the patient-related data, and on one or more time stamps of a previous registration event performed by the registration device, as described herein. Embodiments of how the host system may use the time stamps to make this association will be described in greater detail below.

Subsequently, in step S314, the host system may add the received patient-related data, optionally together with the associated identifiers of the operator and/or the electronic device, to a patient record associated with the patient identifier to which the host system has associated the patient-related data. Additionally or alternatively, the host system may forward the results to a different system for storage and/or further processing.

Figure 4:
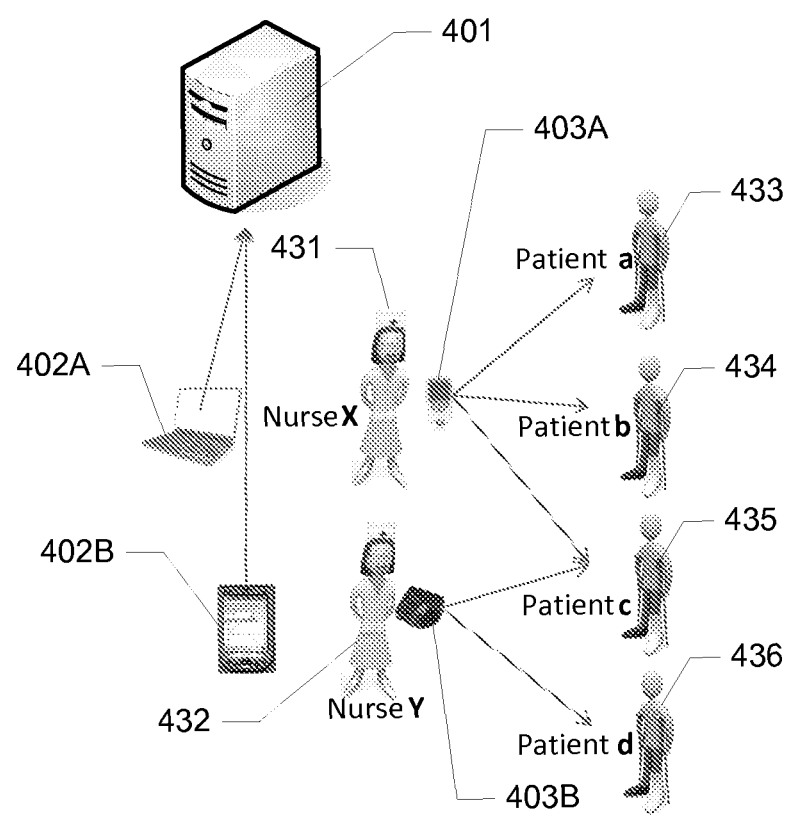
FIG. 4 illustrates an example of the operation of an embodiment of a system for acquiring patient-related data.

FIG. 4 illustrates an example of the operation of an embodiment of a system for acquiring patient-related data. In this example, the system is operated by nurses X and Y (designated by reference numerals 431 and 432, respectively) of a hospital to obtain measurements to be associated with patients a-d, designated by reference numerals 433-436, respectively. In this example, nurse X carries electronic device 403A, while nurse Y carries electronic device 403B. The system further comprises host system 401 and registration devices 402A and 402B connected to the host system 401.

In the following, an exemplary process of obtaining the measurements will be described as a sequence of steps 1) through 17):

1) Nurse X takes Device 403A from, e.g., its docking station (not explicitly shown in FIG. 4)
2) Nurse X scans a device identification barcode of device 403A, and her own barcode using the registration device 402A.
   a) The registration device 402A connected to the host system 401 determines, based on the scanned barcodes, whether device 403A is in compliance, and issues a warning if device 403A is not in compliance (e.g., due to missing quality control activities) or if nurse X is not trained or retraining is overdue.
   b) If the device 403A and nurse X are in compliance, device 403A may be used for testing, and the process continues.
3) Nurse X performs a measurement on patient a using device 403A.
4) Nurse X scans patient a's barcode using the registration device 402A.
5) Nurse Y takes Device 403B from e.g., its docking station.
6) Nurse X performs steps 2, 3 and 4 for Patient b, using registration device 402A and electronic device 403A.
7) Nurse X performs steps 2, 3 and 4 for Patient c using registration device 402A and electronic device 403A.
8) Nurse Y performs step 2 on Device 403B and using registration device 402B.
9) Nurse Y performs a measurement on Patient c, using Device 403B.
10) Nurse Y scans Patient c using the registration device 402B.
11) Nurse Y performs steps 8, 9 and 10 on Patient d.
12) Nurse X returns device 403A to its docking station.
13) Nurse Y returns device 403B to its docking station.
14) Device 403A establishes a connection with the host system (via its docking station) and sends three messages with measuring results to the host system. Each of the messages includes the following information:
   a) Sample time T(acq) (i.e. the time at which the measurement result has been obtained)
   b) Device ID dId identifying the electronic device used to obtain the measurement result
   c) Measurement result PD
15) Device 403B establishes a connection with the host system (via its docking station) and sends two messages with measuring results to the host system. Each of the messages includes the above specified information, i.e. sample time, device ID, and measurement result.
16) The host system 401 maps the sample times and device IDs received in the messages from Devices 403A and 403B, respectively, with the time-of-scanning time stamps, and device ID's obtained by the scanning performed in steps: 2, 4, 6, 7, 8, 10 and 11, thereby associating the measurement data to the patient IDs.

17) The host system stores the five measurement results with the corresponding patient identifiers of patients a-d, respectively, and/or forwards the results to a separate system for storage and/or further processing.

It will be appreciated that the sample time stamp T(acq) and the Device ID dId together generate a unique identifier allowing the host system to associate the measurement data to the scanned barcodes.

By performing two of the ID registration steps prior to the actual measurement and by performing the patient registration after the measurement, the host system may create a time interval within which the host system can map the measurement belonging to the registration.

For example, in the above example of FIG. 4, steps 2), 3), 4), and 6) result in the following sequence of registrations:
1) Scan operator ID (Nurse X)
2) Scan device ID (Device 403A)
3) Perform measurement (Patient a)
4) Scan Patient ID (Patient a)
5) Scan operator ID (Nurse X)
6) Scan device ID (Device 403A)
7) Perform measurement (Patient b)
8) Scan Patient ID (Patient b)

Hence, upon receipt of the time stamps identifying the timing of the above registrations, the host system may establish a first time interval from the earliest to the latest ID scan associated with the measurement on patient a, i.e., from registration 1) to registration 4). Similarly, the host system may establish a second time interval from the earliest to the latest ID scan associated with the measurement on patient b, i.e., from registration 5) to registration 8). From the time stamps of measurements 3) and 7), respectively, the host system may thus determine that the measurement on patient a (registration 3)) was performed in the time interval between registrations 1) and 4), and thus associate the measurement on patient a with the patient ID registered in registration 4). Similarly, the host system may associate the measurement on patient b (registration 7)) with the patient ID obtained in registration 8).

It will be appreciated that, in the above embodiments, the above association does not require a particular sequential order in which the operator ID, the device ID, and the patient ID are scanned, as long as the measurement is performed after the scanning of the first one of the IDs and before the scanning of the last one of the IDs. Furthermore, it will be appreciated that the scanning of the operator ID is not even required for the host system to be able to establish a time interval and to associate the measurement with a patient ID. However, by scanning the operator ID and the device ID before the measurement, a compliance check may be performed as described above.

In the following, alternative methods of associating the measurement with a patient ID based on the registered identifiers and times will be described with reference to FIGS. 5 and 6 below.

With continued reference to FIG. 4, in some embodiments, when connected to the host system 401, the following information is included in all messages from the electronic devices 403A and 403B, respectively:
1) Device ID
2) Current transmission time—e.g., the time as it is setup on the instrument.

If there is a difference between the current transmission time as received by the host system and the current time determined by the host system, the host system may try to automatically adjust the device time of the electronic device (if such functionality is supported by the electronic device) and/or save the time difference in the database. Due to the above comparison of the device time and the time determined by the host system, any time a message is received from that electronic device, the host system can determine the exact time of measurement.

Some electronic devices may use only hour and minutes as timestamp and since the time required by each measurement may be shorter (some devices may allow 1-3 measurements per minute) it is possible that two measurements can have the same timestamp. Upon registration of an electronic device by the registration device, the registration device may retrieve information about such limitations of the electronic device, and the registration device may inform the user that there is a potential risk of not automatically being able to identify a patient sample with the registrations performed if two registrations are performed within 60 seconds. In case a user disregards the warning and performs two measurements with same timestamp, the host system may later query for either performing a sample rerun or that the user manually maps the patient ID with the measurement. Generally, embodiments of the system described herein may detect situations that involve a risk of incorrect associations, e.g., due to limited time resolution of the timers, and perform an appropriate action so as to avoid any inadvertent associations.

Figure 5:
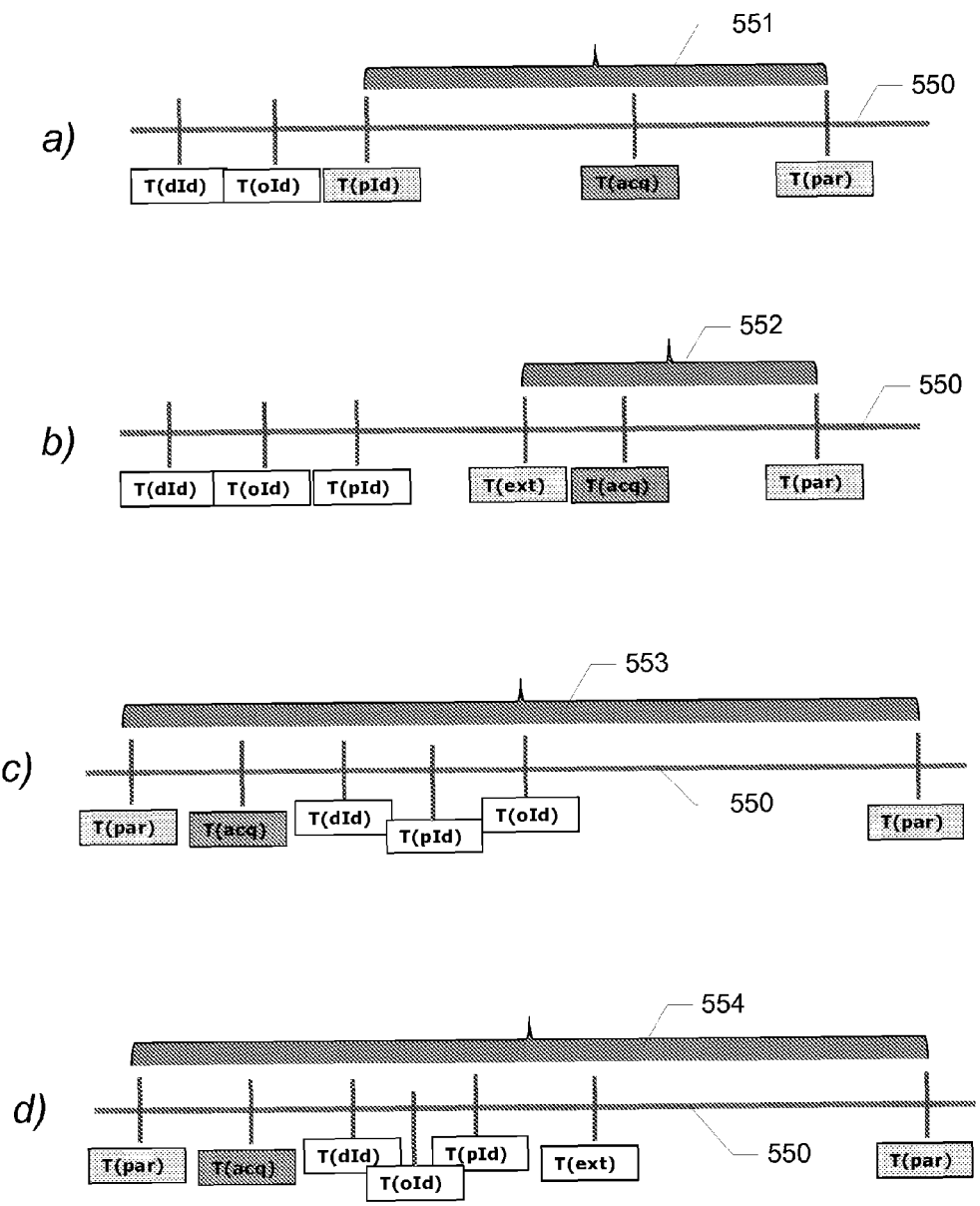
FIGS. 5 and 6 illustrate different embodiments of a method of acquiring patient-related data.
Figure 6:
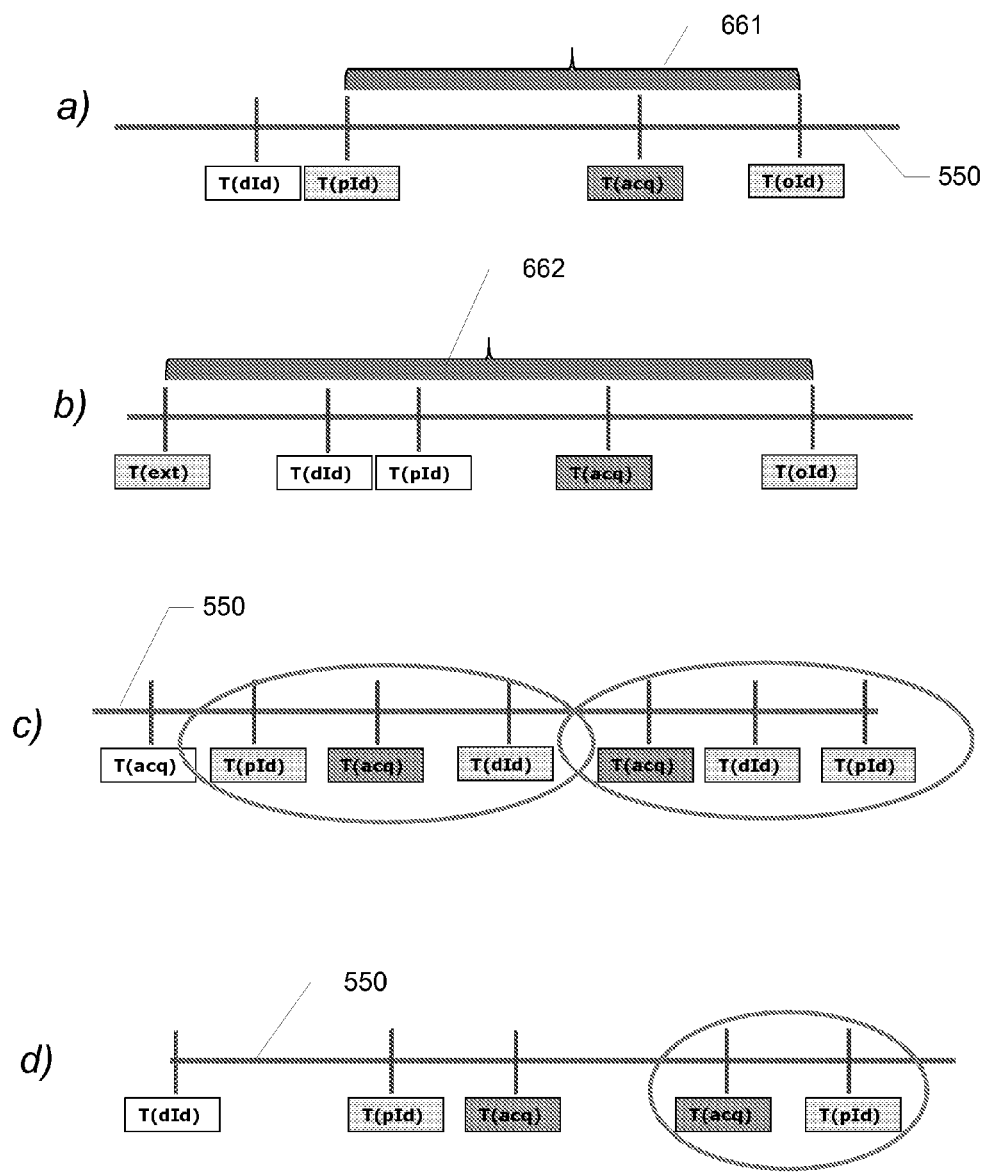

FIGS. 5 and 6 illustrate different embodiments of a method of acquiring patient-related data. In particular, FIGS. 5a-d and FIGS. 6 a-d each illustrate a time line 550, and the sequential order of different registration events. In the following, the following notation will be used:
T(pId)=Time stamp of patient identification by the registration device
T(dId)=Time stamp of the electronic device identification by the registration device
T(oId)=Time stamp of the operator identification by the registration device
T(acq)=Time stamp of the data acquisition (measurement) performed by the electronic device
T(ext)=Time stamp of an external trigger event
T(par)=Time stamp of a computerized parameter
$\Delta T(x,y)$=Time interval between two time stamps y and x (where y is an older event than x), e.g., $\Delta T(pId,dId)$ =Time interval between T(dId) and T(pId)

For the purpose of the following description, it is assumed that the identifiers are in the form of machine readable codes that can be scanned by the operator using the registration device, and that the patient-related data relates to measurements. However, it will be appreciated that any other form of obtaining the identifiers may be used, and that the patient-related data may be indicative of data other than measurements. Furthermore, in the following examples, some assumptions under which the host system performs the association between measurements and patient identifiers are specified. During operation of the system, compliance with these assumptions may e.g., be ensured by suitable standard operating procedures instructing the operators about how to operate the system.

Generally the process of associating the received patient-related data with a patient identifier may initially determine one or more received sets of identification data items where each set comprises a device identification data item that matches the obtained device identifier of the electronic device from which the patient-related data has been received. The process may then associate the received patient-related data with the patient identification data item of one of the determined sets of identification data items based on at least the received one or more identification time stamps and the received acquisition time stamp as described in greater detail below.

In the example of FIG. 5a the host system determines a registration time interval based on an assumption that the operator scans the electronic device ID, the operator ID, and the patient ID, and subsequently performs the measurement using the electronic device. After receipt of the three identifiers, the registration device blocks the registration device to be used for a new session (i.e., further scans of identifiers) until a predetermined time interval (e.g., of 3 minutes) has elapsed starting from the receipt of the last of the three scans. In FIG. 5a, the end of the time-out period is labeled by the time T(par), e.g., as determined by expiry of a timer of the registration device. The host system subsequently determines the time interval $\Delta T(par, pId)$ (designated by reference numeral 551) between the scanning of the patient ID and the expiry of the timer T(par). The host system then identifies a measurement originating from the electronic device with device ID dId and where the measurement has a time stamp T(acq) within the time interval $\Delta T(par, pId)$. Alternatively, the host system may determine the time interval as the time starting from the earliest of the group of three scans and ending at T(par). The group of scans including the operator ID, device ID and patient ID relating to the same registration event may be determined by the host system as a group received within the same message from the registration device, or as a group determined by the host system from the overall sequence and/or relative timing of received identifiers.

The example of FIG. 5b is similar to that of FIG. 5a. However, in this example the acquisition time interval 552 is not triggered by one of the scans but by a predetermined external event at time T(ext), e.g., by the operator pressing a predetermined button (or performing another predetermined action) on the registration device. For example, the operator may scan the three identifiers and then press a "start" button which causes the registration device to forward a message to the host system including the three scanned identifiers and a single time stamp T(ext) indicative of the time at which the user has pressed the "start" button. Furthermore, the registration device may block the system for a predetermined time interval until T(par) so as to prevent scanning of further identifiers during the time interval for measurement. The host system subsequently determines the time interval $\Delta T(par, ext)$ (designated by reference numeral 552) between the external event and the expiry of the timer T(par). The host system then identifies a measurement originating from the electronic device with device ID dId and where the measurement has a time stamp T(acq) within the time interval $\Delta T(par, ext)$.

The example of FIG. 5c is similar to that of FIG. 5a but where the acquisition time interval extends to both sides of the scan that triggers the time interval. In the example of FIG. 5c the host system determines a registration time interval based on an assumption that the operator scans the electronic device ID, the operator ID, and the patient ID, and performs the measurement using the electronic device within a predetermined time interval after or prior to the scanning of the identifiers. To this end, after receipt of the three identifiers, the registration device blocks the registration device to be used for a new session (i.e. further scans of identifiers) until a predetermined time interval (e.g., of 3 minutes) has elapsed starting from the receipt of the last of the three scans.

The host system subsequently determines the time interval 553 to extend a predetermined period prior to the last one of the three scans and a predetermined period after the last scan, where the length of each predetermined period may be selected to be equal to the length of the blocking period. Hence, the system assumes (or checks based on data received from the registration device) that the system was not blocked during the predetermined period prior to the last scan. The host system then identifies a measurement originating from the electronic device with device ID dId and where the measurement has a time stamp T(acq) within the time interval 553. In one embodiment, if multiple such measurements are identified, only the most recent one is considered. Alternatively, the system may cause a rerun of the measurement process, e.g., after issuing an error message.

The example of FIG. 5d is similar to that of FIG. 5c in that the time interval 554 extends to both sides of the triggering event. However, in this example, the time interval 554 is triggered by an external event (e.g., by a user pressing a given button on the registration device) rather than by one of the scans, i.e., similar to the triggering described in the example of FIG. 5b.

In the example of FIG. 6a the host system determines a registration time interval based on an assumption that the operator initially scans the device ID of the electronic device, and the patient ID, then performs the measurement using the electronic device, and finally scans the operator ID. This scenario is similar to the example described with reference to FIG. 4 above. In particular, the host system determines the time interval $\Delta T(oId, pId)$ (designated by reference numeral 661) between the scanning of the patient ID and the scanning of the operator ID. The host system then identifies a measurement originating from the electronic device with device ID dId and where the measurement has a time stamp T(acq) within the time interval $\Delta T(oId, pId)$. Alternatively, the host system may determine the time interval as the time from the earliest to the latest of a group of three scans of the operator ID, device ID and patient ID relating to the same registration event (e.g., as a group received from the registration device, or as a group determined by the host system from the overall sequence and/or relative timing of received identifiers).

In the example of FIG. 6b, the measuring process is assumed initiated by an external event, such as, the receipt by the registration device (e.g., via the host system) of a test order from a Hospital Information System (HIS). In response to the external event, the operator is assumed to scan the device ID and the patient ID. Then the operator is assumed to perform the measurement using the electronic device, and finally to scan the operator ID. In this example the host system determines the time interval 662 between the time T(ext) at which the external event has occurred, and the latest of the three expected scans of identifiers, in this case the scan of the operator ID. The host system then identifies a measurement originating from the electronic device with device ID dId and where the measurement has a time stamp T(acq) within the time interval $\Delta T(oId, ext)$.

In the example of FIG. 6c, the host system does not receive any operator ID from the registration device, but merely a patient ID and a device ID as well as their associated time stamps. The operator is thus assumed to scan the patient ID and the device ID, and to perform a measurement. These actions may be performed in any order; however, the subsequent association is based on the assumption that each registration/measuring event comprises at least a patient ID, a device ID, and a measurement. In this example the host system associates the received measurements with respective patient IDs based on a sequential grouping of the registration and measuring events. The host system may, based on the sequential order of the corresponding time stamps, iteratively identify groups, each group comprising a patient ID, a device ID and a measurement, as illustrated in FIG. 6c. For example, in each iteration, the host system may identify the earliest time stamp that has not yet been assigned to a group, and assign this time stamp to a new group. Subsequently, the host system may identify the earliest time stamps that are subsequent to the initially identified time stamp, and add them to the new group until the group consists of a time stamp associated with a patient ID, a time stamp associated with a device ID, and a time stamp associated with a measurement. It will be appreciated that this embodiment may be modified to also comprise operator IDs. In such an embodiment, each group is determined, based on their respective time stamps, as a group comprising a patient ID, a device ID, an operator ID, and a measurement.

The example of FIG. 6d is similar to FIG. 6c, in that the association of measurements to patient devices is based on a determination of groups of registration/measurement events based on the respective time stamps. However, in this embodiment, the grouping is only based on the time stamps of the registered patient IDs and the time stamps of the measurements. The operator is assumed to only register the device ID once (e.g., in the morning when the operator starts working with the corresponding electronic device, or every time the operator switches to a new electronic device). Subsequently, the operator only needs to scan the patient ID and perform a measurement with the previously registered electronic device. In this example the host system associates the received measurements with corresponding patient IDs based on the initially registered device ID, and based on a sequential grouping of the registration and measuring events. The host system may, based on the sequential order of the corresponding time stamps, iteratively identify groups, each group comprising a patient ID and a measurement, as illustrated in FIG. 6d. It will be appreciated that this embodiment may be modified to also comprise operator IDs. In such an embodiment, the operator may perform an initial registration of both the device ID and the operator ID, thus allowing the registration device to perform a compliance test. Subsequently, the operator merely performs registrations of the respective patient IDs and performs measurements. It will further be appreciated that also some of the other examples described above may be modified in that the device ID and/or the operator ID does not need to be registered in connection with every measurement, but only during an initial start-up and/or upon a change in operator and/or electronic device. For example, in the examples of FIGS. 5a through 5d, as well as 6a and 6b, the definition of time intervals may be based on the patient ID and/or an external event.

Hence the above examples illustrate that a unique identification of an acquisition time stamp T(acq) to be associated with a patient identification may be based on one or more time stamps associated with the registration of one or more identifiers and on the patient identifier and the device identifier. Generally, in a first group of embodiments, the association is based on an identification of a time interval ΔT(x,y) in order to constrain T(acq) inside the boundaries of the interval, i.e., identify the correct acquisition time stamp as the one that falls within the identified time interval. In a second group of embodiments, the association is based on an identification of a group of actions and an association of the identified group with T(acq). The identification of the group and the linking of T(acq) to the group may be based on the sequential order of the actions and/or their relative timing, and on the relative timing of T(acq) relative to the members of the identified group. The group may include at least the registration of the patient ID.

It will be appreciated that a system implementing an embodiment of the method described herein may be configured to implement one or more embodiments, e.g., including one or more embodiments described above. In particular, such a system may be adapted to allow an operator to select one of a set of available embodiments. For example such a selection may be performed during an initial configuration of the system, thus allowing adaptation of the system to the capabilities of the devices available at a given healthcare facility and/or to existing standard operating procedures at that healthcare facility. In particular, the system may allow an operator to select a mode of operation from a plurality of available modes of operation. A mode of operation may e.g. be identified by the association criteria to be used (e.g., based on time intervals or on the sequential order of trigger events, etc.) and by an identification of which types of time stamps or other triggers to be used during that association.

For example, to configure such a configurable system to implement the embodiment described in connection with FIG. 5a, an operator may select an association based on time intervals from a list of types of association criteria. In a subsequent step, the operator may select receipt of a patient ID time stamp as a start trigger for a time interval, and the expiry of a timer (e.g., of configurable duration) as a termination trigger for the time interval. The selection of the trigger may be performed as a selection from a list of available triggers. A list of association criteria may, e.g., include "one-sided time interval with start trigger", "two-sided time interval with central trigger", "identification of groups of events", etc. A list of available start or termination triggers may e.g. include "patient ID time stamp", "device ID time stamp", "operator ID time stamp", "external event", "timer", and/or the like.

It will be appreciated that such a configuration may be performed in a variety of different ways, e.g. at run-time during an initial configuration or set-up stage where an operator may be presented with a sequence of user interface elements allowing the operator to select the configurable modes of operation. Alternatively, the configuration may be performed prior to the initial operation of the system, e.g. by means of creating a configuration file that includes the relevant configuration parameters, or even at compile time of a corresponding software application.

Although some embodiments have been described and shown in detail, the invention is not restricted to them, but may also be embodied in other ways within the scope of the subject matter defined in the following claims.

The method, product, system, and device described herein can be implemented by hardware comprising several distinct elements, and/or partly or completely by a suitably programmed microprocessor. In the device claims enumerating several items, several of these items can be embodied by one and the same item of hardware, e.g., a suitably programmed microprocessor, one or more digital signal processor, or the like. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

It will be apparent to those skilled in the art that various modifications and variations can be made in the method and system for acquiring patient-related data of the present invention without departing from the spirit or scope of the invention. Thus, it is intended that the present invention cover the modifications and variations of this invention provided they come within the scope of the appended claims and their equivalents.

What is claimed is:

1. A method, performed by a data processing system, of registering patient-related data, the method comprising:
   receiving, from a registration device, a set of identification data items and one or more identification time stamps, wherein each identification time stamp is associated with at least one of the identification data items, and the set of identification data items comprises a device identification data item identifying an electronic device and a patient identification data item identifying a patient;
   receiving, from the electronic device, patient-related data to be registered and an acquisition time stamp indicative of an acquisition time at which the patient-related data has been acquired; and
   associating, by the data processing system, the received patient-related data with an identified patient based on at least the received device identification data item, the received patient identification data item, the received one or more identification time stamps and the received acquisition time stamp.

2. The method according to claim 1, wherein the associating the received patient-related data with the identified patient comprises comparing the acquisition time with a first time identified by a first one of the one or more identification time stamps.

3. The method according to claim 2, wherein the comparing the acquisition time with the first time comprises determining whether the acquisition time lies within a predetermined data acquisition time interval determined from at least the first identification time stamp, and the associating received patient-related data with an identified patient comprises associating the patient-related data with the patient identification data item if the acquisition time lies within the predetermined data acquisition time interval.

4. The method according to claim 3, wherein the data acquisition time interval is a time interval starting at the first time and having a predetermined length.

5. The method according to claim 3, wherein the data acquisition time interval extends a first predetermined period prior to the first time and a second predetermined period after the first time.

6. The method according to claim 3, wherein the receiving the set of identification data items and one or more identification time stamps comprises receiving at least the first and a second identification time stamp, the second identification time stamp identifying a second time, and wherein the data acquisition time interval is a time interval starting at the first time and ending at the second time.

7. The method according to claim 6, wherein the second time is an identification time at which one of the identification data items has been obtained.

8. The method according to claim 6, wherein the second time is a time at which a predetermined trigger event has occurred.

9. The method according to claim 2, wherein the first time is a time at which a predetermined trigger event has occurred.

10. The method according to claim 2, wherein the first time is an identification time at which one of the identification data items has been obtained.

11. The method according to claim 2, wherein the receiving the set of identification data items comprises receiving a plurality of identification data items and determining the set of identification data items from the received plurality of received identification data items as a set of identification data items associated with the first identification time stamp.

12. The method according to claim 11, wherein the determining the set of identification data items comprises determining a set of obtained identification data items from at least one of a sequential order in which the identification data items have been obtained and a relative timing of respective identification times at which the respective identification data items have been obtained.

13. The method according to claim 1, wherein each of the one or more identification time stamps is indicative of an identification time at which a respective one of the identification data items has been obtained, and
   wherein associating comprises comparing a sequence of identification time stamps and a sequence of data acquisition time stamps, and identifying associated sets of identification events and data acquisition events from the comparison.

14. The method according to claim 13, wherein the identification time stamps comprise a patient identification time stamp and a device identification time stamp, the patient identification time stamp being indicative of a patient identification time at which the patient identification data item has been obtained, and the device identification time stamp being indicative of a device identification time at which the device identification data item has been obtained, and
   wherein identifying associated sets of identification events and data acquisition events comprises identifying triplets of respective patient identification time stamps, device identification time stamps, and data acquisition time stamps.

15. The method according to claim 13, wherein the identification time stamps comprise a patient identification time stamp indicative of a patient identification time at which the patient identification data item has been obtained, and
   wherein identifying associated sets of identification events and data acquisition events comprises identifying duplets of respective patient identification time stamps and data acquisition time stamps.

16. The method according to claim 1, wherein the set of identification data items further comprises an operator identification data item identifying an operator of the electronic device.

17. The method according to claim 1, wherein the receiving the acquisition time stamp from the electronic device further comprises receiving, from the electronic device, a control time stamp indicative of a current time determined by the electronic device, and correcting the acquisition time stamp based on a comparison of the control time stamp with a current time determined by the data processing device.

18. The method according to claim 1, wherein the receiving patient related data to be registered and an acquisition time stamp further comprises obtaining a device identifier of the electronic device from which the patient-related data is received, and
   wherein the associating the received patient-related data with an identified patient is further based on the obtained device identifier of the electronic device from which the patient-related data is received.

19. A data processing system for registering patient-related data, comprising:
   a communications interface configured to receive, from a registration device, a set of identification data items and one or more identification time stamps, wherein each identification time stamp is associated with at least one of the identification data items, and the set of identification data items comprises a device identification data item identifying an electronic device and a patient identification data item identifying a patient, and further configured to receive, from the electronic device, patient-related data to be registered and an acquisition time stamp indicative of an acquisition time at which the patient-related data has been acquired; and a processor configured to associate the received patient-related data with an identified patient based on at least the received device identification data item, the received patient identification data item, the received one or more identification time stamps and the received acquisition time stamp.

20. A system for registering patient-related data, comprising:
   a registration device;
   an electronic device; and
   a data processing system comprising a first communications interface configured to receive, from the registration device, a set of identification data items and one or more identification time stamps, wherein each identification time stamp is associated with at least one of the identification data items, and the set of identification data items comprises a device identification data item identifying an electronic device and a patient identification data item identifying a patient, and further configured to receive, from the electronic device, patient-related data to be registered and an acquisition time stamp indicative of an acquisition time at which the patient-related data has been acquired; and a processor configured to associate the received patient-related data with an identified patient based on at least the received device identification data item, the received patient identification data item, the received one or more identification time stamps and the received acquisition time stamp,
   wherein the registration device comprises an input configured to receive an identifier, and a second communications interface configured to forward an identification data item indicative of the received identifier to the data processing system, and wherein the electronic device comprises a patient-related data acquisition unit, and a third communications interface configured to communicate the acquired patient-related data to the data processing system.

21. A registration device for use with a data processing system configured to receive a set of identification data items and one or more identification time stamps from the registration device, wherein each identification time stamp is associated with at least one of the identification data items, and the set of identification data items comprises a device identification data item identifying an electronic device and a patient identification data item identifying a patient; and configured to receive, from the electronic device, patient-related data to be registered and an acquisition time stamp indicative of an acquisition time at which the patient-related data has been acquired; and associates the received patient-related data with an identified patient based on at least the received device identification data item, the received patient identification data item, the received one or more identification time stamps and the received acquisition time stamp, the registration device, comprising:
   an input configured to receive a set of identifiers each identifying a respective object;
   a communications interface configured to communicate an identification data item for each received identifier to the data processing system, the identification data item comprising the identifier and an identification time stamp indicative of an identification time at which the object has been identified; and
   a processing unit configured to prevent for a period of time after receipt of the set of identifiers communicating further identification data items including identifiers different from the set of received identifiers.

22. A non-transitory computer readable storage medium storing instructions that when executed by a processor comprise:
   receiving, from a registration device, a set of identification data items and one or more identification time stamps, wherein each identification time stamp is associated with at least one of the identification data items, and the set of identification data items comprises a device identification data item identifying an electronic device and a patient identification data item identifying a patient;
   receiving, from the electronic device, patient-related data to be registered and an acquisition time stamp indicative of an acquisition time at which the patient-related data has been acquired; and
   associating the received patient-related data with an identified patient based on at least the received device identification data item, the received patient identification data item, the received one or more identification time stamps and the received acquisition time stamp.

* * * * *